United States Patent [19]

Hübner-Parajsz et al.

[11] Patent Number: 5,817,469
[45] Date of Patent: Oct. 6, 1998

[54] MONOCLONAL ANTIBODIES AGAINST CK-MB

[75] Inventors: Christa Hübner-Parajsz, Tutzing; Ulrich Essig, Planegg; Fridl Lang, Tutzing; Rudolf Vogel, Weilheim, all of Germany

[73] Assignee: Boehringer Mannheim GmbH, Mannheim, Germany

[21] Appl. No.: 535,058

[22] PCT Filed: Apr. 28, 1994

[86] PCT No.: PCT/EP94/01337

§ 371 Date: Oct. 30, 1995

§ 102(e) Date: Oct. 30, 1995

[87] PCT Pub. No.: WO94/25617

PCT Pub. Date: Nov. 10, 1994

[30] Foreign Application Priority Data

Apr. 30, 1993 [DE] Germany .......................... 43 14 254.0

[51] Int. Cl.⁶ .................................................. G01N 33/573
[52] U.S. Cl. ...................... 435/7.4; 435/7.92; 435/7.94; 436/531; 436/533; 436/548; 530/388.26
[58] Field of Search ..................................... 435/7.4, 7.92, 435/17, 973; 436/518, 531, 533, 547, 548, 810, 811, 819; 530/388.1, 388.26, 389.1, 389.3

[56] References Cited

U.S. PATENT DOCUMENTS

| 4,376,110 | 3/1983 | David et al. | 436/513 |
|---|---|---|---|
| 4,912,033 | 3/1990 | Ladenson et al. | 435/7.4 |
| 5,382,515 | 1/1995 | Shah et al. | 435/74 |

FOREIGN PATENT DOCUMENTS

| 9304374 | 4/1993 | WIPO | 435/7.4 |

OTHER PUBLICATIONS

Eisenburg et al., "Concordance of Creativie Kenase –MB Activity and Mass," Clinical Chemistry 35(3):440–443, 1989.

Badminton et al., "Evaluation of a new rapid immunometric method for the measurement of the MB isoenzyme . . . " Ann. Clin. Biochem. 29:563–4, 1992.

Landt et al., "Semi–Automated Direct Colormetric Measurement of Creative Kinase Isonzyme MB . . . by Use of a CK–MB–Specific Monoclonal Antibody" Clin Chem. 34:575–81, 1988.

Landtt et al., "Immunaffinity Purification . . . with Use of a Monoclonal Antibody specificator CK–MB," Clin. Chem. 35:985–89, 1989.

Lanidou et al., "Assay of Creative Kinase Isoenzyme MB . . . " Clin. Chem. 36:1679–83, 1990.

Mühlabach et al., "Sequence homology and structure predictions of the creative kinase isoenzymes," Mol. Cell. Biochem. 133/134:245–262, 1994.

Piran et al., "Immunochemilumenometric Assay of Creative Kinase MB with a Monoclonal Antibody to the MB Isoenzyme," Clin. Chem. 33:1517–20, 1987.

Vaidya et al., "Direct Measurement of Creative Kinase–MB Activity in Srum . . . with a Monoclonal Antibody Specific to the MB Isoenzyme," Clin. Chem. 32:657–63, 1986.

*Primary Examiner*—Carol A. Spiegel
*Attorney, Agent, or Firm*—Nikaido Marmelstein Murray & Oram LLP

[57] ABSTRACT

The invention concerns monoclonal antibodies which bind to the CK-MB isoenzyme but not to the B or M subunit of CK-MB or to the CK-MM and CK-BB isoenzmyes, as well as a method for the diagnostic detection of CK-MB in a homogeneous diagnostic test using these antibodies.

4 Claims, No Drawings

MONOCLONAL ANTIBODIES AGAINST CK-MB

This application is a filing under 35 U.S.C. § 371 of PCT/EP 94/1337 filed on Apr. 28, 1994.

FIELD OF THE INVENTION

The invention concerns monoclonal antibodies which bind to the CK-MB isoenzyme but not to the B or M subunit of CK-MB or to the CK-MM and CK-BB isoenzymes, as well as a method for detecting CK-MB in a diagnostic test using these antibodies.

DESCRIPTION OF RELATED ART

Creatine kinase (ATP: creatine-N-phosphotransferase, EC 2.7.3.2) catalyzes the reversible phosphorylation of creatine in the presence of ATP to creatine phosphate. The enzyme is composed of two subunits of which an M (muscle-specific) and B (brain-specific) form is known which have a homology to one another of 78.7 %. The dimeric enzyme is composed either of two identical subunits (muscle-specific CK-MM isoenzyme and brain-specific CK-BB isoenzyme) or is present as a heterodimer. This heterodimeric CK-MB isoenzyme is specific for heart muscle and is detectable in serum above all in the case of injured myocardium e.g. cardiac infarction, a progressive muscular dystrophy or toxic myopathies. Due to its high specificity, the determination of CK-MB in serum is an important emergency parameter for diagnosis of a cardiac infarction. Therefore several methods for the determination of CK-MB in serum have already been described in which CK-MB is detected by an electrophoretic or ion-chromatographic separation, by a radioimmunoassay or an enzymatic determination of activity while inhibiting the M subunit with an antibody. These methods are, however, very time consuming. Since the determination of CK-MB is important particularly in emergency situations, a suitable test must not only be specific for CK-MB but capable of being carried out rapidly.

Immunoassays have therefore also been described in which CK-MB is detected by a sandwich assay using antibodies against CK-MM and CK-BB. Although theoretically only CK-MB should be detectable by this means, such a sandwich assay has proven to be very susceptible to interference by CK-MM and CK-BB since anti-CK-MM antibodies also cross-react with CK-BB and anti-CK-BB antibodies also cross-react with CK-MM. Therefore such a sandwich assay easily leads to false-positive results. Specific monoclonal antibodies for CK-MB were also developed by Vaidya et al. (Clin. Chem. 32, 1986, 657–663). One of these antibodies was characterized particularly well. This antibody is denoted the so-called "Conan" antibody and is considered to be a reference antibody for monoclonal antibodies against CK-MB. However, this and also a series of other monoclonal antibodies against CK-MB which have been developed in the meantime only have a low affinity to CK-MB and moreover all recognize the same epitope, the so-called "Conan" epitope of CK-MB, so that no sandwich immunoassay is possible with these antibodies.

In the previously described sandwich immunoassays only one CK-MB-specific monoclonal antibody is used. The second antibody is an antibody against the M or B subunit and thus also recognizes CK-MM or CK-BB.

SUMMARY OF THE INVENTION

The object of the invention was therefore to provide monoclonal antibodies against the CK-MB isoenzyme which do not bind to the CK-MM and CK-BB isoenzymes.

DESCRIPTION OF THE PREFERRED EMBODIMENTS

This object is achieved by a monoclonal antibody which binds to the CK-MB isoenzyme but not to the B or M subunit alone of CK-MB or substantially to the CK-MM or CK-BB isoenzymes, the binding to CK-MB taking place in an equivalent manner to the binding of the monoclonal antibodies DSM ACC 2058, DSM ACC 2060 or DSM ACC 2168. This monoclonal antibody is obtainable by immunizing A/J mice (H-$2^a$ haplotype) with the CK-MB isoenzyme using aluminium hydroxide as an adjuvant, immortalizing the spleen cells of the immunized mice and cloning those immortalized cells which produce an antibody which binds to CK-MB but not to CK-MM or CK-BB and which is not displaced from the binding to CK-MB by the "Conan MB antibody" (ATCC HB 8939).

Such an antibody which reacts specifically with CK-MB but not substantially with CK-MM or CK-BB must recognize a conformation epitope which is formed by the M as well as by the B subunit. Since the binding region of an antibody recognizes about 6 to 10 amino acids of the antigen as an epitope, the two subunits of CK-MB each contribute about 5 amino acids to this conformation epitope. In addition due to the steric configuration of the amino acid side chains as well as their hydrophilicity, only particular sections of a protein sequence are immunogenic. Hence dimeric antigens usually only have a very low number of conformation epitopes, both subunits mutually contributing to their specificity. It was therefore surprising that is was possible to find monoclonal antibodies against the CK-MB isoenzyme which recognize four different conformation epitopes on the CK-MB isoenzyme and are thus suitable for a sandwich assay or even for a triplet formation. These four epitopes are characterized by the binding of the "Conan MB antibody" ATCC HB 8939 as well as of the monoclonal antibodies DSM ACC 2059 and/or DSM ACC 2057 according to the invention for the first epitope, by the binding of the antibody DSM ACC 2058 for the second epitope, by the binding of the antibody DSM ACC 2060 for the third epitope and by the binding of the antibody DSM ACC 2168 for the fourth epitope.

It surprisingly turned out that the antibodies DSM ACC 2058, DSM ACC 2060, DSM ACC 2057, DSM ACC 2059 and DSM ACC 2168 have higher association constants for binding to CK-MB than the previously known monoclonal antibodies against CK-MB. These monoclonal antibodies therefore react very rapidly with CK-MB and are thus particularly suitable for rapid diagnostic tests.

Therefore a monoclonal antibody against the CK-MB isoenzyme according to the invention is preferred which has an association constant for binding to CK-MB of at least $1 \times 10^5$ mol$^{-1} \times 1 \times$sec$^{-1}$.

The monoclonal antibodies according to the invention are preferably of the IgG1 isotype.

The monoclonal antibodies according to the invention against CK-MB can be combined in any manner with one another as well as with known antibodies against CK-MB for a sandwich immunoassay for the detection of CK-MB provided that two antibodies are used which recognize a different epitope on CK-MB. The antibodies according to the invention can of course also be combined with antibodies against the M or B subunit of creatine kinase.

For a test which is as sensitive as possible the antibodies should in addition have a high affinity to CK-MB. It has surprisingly turned out that the aforementioned monoclonal antibodies DSM ACC 2059 and DSM ACC 2057 have a higher affinity constant than the previously known antibodies against this epitope of CK-MB.

The invention therefore also concerns a monoclonal antibody which binds to the CK-MB isoenzyme but not to the B or M subunit alone of CK-MB or not substantially to the CK-MM and CK-BB isoenzymes, the binding to CK-MB taking place in an equivalent manner to the binding of the monoclonal antibodies DSM ACC 2057 or DSM ACC 2059, which has an affinity constant of at least $1\times10^8$ mol$^{-1}\times$1 to CK-MB. This monoclonal antibody is obtainable by immunizing A/J mice (H-$2^a$ haplotype) with the CK-MB isoenzyme using aluminium hydroxide as an adjuvant, immortalizing the spleen cells of the immunized mice and cloning those immortalized cells which produce an antibody which binds to CK-MB but not substantially to CK-MM or CK-BB, which is displaced by the "Conan MB antibody" (ATCC HB 8939) from the binding to CK-MB and has an affinity constant of at least $1\times10^8$ mol$^{-1}\times$1 to CK-MB. The determination of the affinity constant is carried out by means of the BIAcore® system (Pharmacia LKB) using the kinetic evaluation kit software (Pharmacia LKB, Ident.No. BR-1000-19).

The above-mentioned monoclonal antibodies DSM ACC 2057 and DSM ACC 2059 additionally have a dissociation constant of less than $4\times10^{-4}$ sec$^{-1}$. This means that the complex of antibody and CK-MB dissociates again only very slowly. This is important for certain immunologically test methods such as e.g. the IEMA (Immuno Enzyme Metric Assay) since a rapid dissociation of the antibody-CK-MB complex would lead to a competing reaction between binding of the labelled antibody to the analyte and the immobilized antigen and thus to a falsification of the measured value.

A preferred subject matter of the invention is therefore a monoclonal antibody against the CK-MB isoenzyme according to the invention which binds in an equivalent manner to CK-MB as the monoclonal antibody DSM ACC 2057 or DSM ACC 2059 and which has a dissociation constant of less than $4\times10^{-4}$ sec$^{-1}$. Those monoclonal antibodies according to the invention are particularly preferred which additionally have an association constant for binding to CK-MB of at least $1\times10^5$ mol$^{-1}\times$1$\times$sec$^{-1}$.

The antibodies according to the invention can be obtained by immunizing A/J mice (H-$2^a$ haplotype) with the CK-MB isoenzyme. It surprisingly turned out that when this mouse strain is immunized, a substantially higher antibody titre is obtained than with Balb/c mice which are conventionally used for this. In addition it has proven to be particularly advantageous for producing the antibodies according to the invention against a conformation epitope to adsorb the CK-MB for immunization to aluminium hydroxide and Bordetella pertussis. After about four months the spleen cells of the immunized mice are immortalized and those immortalized cells are cloned which produce the desired antibody. The immortalization of the spleen cells is carried out according to methods known to a person skilled in the art; the cells are preferably fused with myeloma cells. Those immortalized cells that produce the desired antibody are identified by a parallel determination of the reactivity of a sample of the culture supernatant with immobilized CK-MB, CK-MM or CK-BB. The desired antibodies against a conformation epitope of CK-MB react with CK-MB but not substantially with CK-MM or CK-BB. The term not substantially means that the reaction with CK-MM and CK-BB is so low that in an immunological test for the detection of CK-MB interferences caused by the presence of CK-MM and CK-BB at their physiological concentration is less than 1% and preferably less than 0.1%. In this case the reaction with CK-MM must be infinitesimal since CK-MM occurs in high concentrations in serum or plasma. Since CK-BB occurs only in very low concentrations in serum or plasma, a slight reaction of the antibodies with this isoenzyme is not relevant. The appropriate immortalized cells are cloned by conventional methods e.g. by separation by means of a fluorescent-activated cell sorter. A competitive test system is used to identify those clones that produce an antibody which binds in an equivalent manner to CK-MB as the monoclonal antibody DSM ACC 2058, DSM ACC 2060 or DSM ACC 2168. For this purpose an enzyme immunoassay is for example used to examine to what extent the antibody competes with the "Conan MB antibody" (ATCC HB 8939) for binding to CK-MB. For this CK-MB is incubated with the "Conan MB antibody" (ATCC HB 8939) in a labelled form and with an excess of the antibody under consideration. Then by immobilizing the complexes formed, separating the solid from the liquid phase and determining the bound label in one of the two phases, it is easy to establish whether the antibody under consideration is displaced from the binding by the "Conan MB antibody" (ATCC HB 8939). If this is not the case, the binding to CK-MB very probably corresponds in an equivalent manner to the binding of the monoclonal antibody DSM ACC 2058, DSM ACC 2060 or DSM ACC 2168.

In order to identify those clones which produce an antibody with the desired association constant or dissociation constant for binding to CK-MB or with the desired affinity to CK-MB, the association constant, dissociation constant or affinity of the antibody formed to CK-MB is then determined in a sample of the culture supernatant. This determination is preferably carried out by means of the BIAcore® system (Pharmacia LKB, Kinetic Evaluation Kit, Ident.No. BR-1000-19). In this manner it was possible to obtain the hybridoma cell lines DSM ACC 2059, DSM ACC 2057, DSM ACC 2058, DSM ACC 2060 and DSM ACC 2168.

A particularly preferred subject matter of the invention are monoclonal antibodies which are obtainable from one of the hybridoma lines DSM ACC 2059, DSM ACC 2057, DSM ACC 2058, DSM ACC 2060 and/or DSM ACC 2168 as well as the said hybridoma lines.

The invention in addition concerns a process for producing monoclonal antibodies which bind to the CK-MB isoenzyme but not to the B or M subunit alone of CK-MB or not substantially to the CK-MM and CK-BB isoenzymes, the binding to CK-MB taking place in an equivalent manner to the binding of the monoclonal antibodies DSM ACC 2058, DSM ACC 2060 or DSM ACC 2168, by immunizing A/J mice (H-$2^a$ haplotype) with the CK-MB isoenzyme using aluminium hydroxide as an adjuvant, immortalizing the spleen cells of the immunized mice, cloning those immortalized cells which produce an antibody which binds to CK-MB but not substantially to CK-MM or CK-BB and which is not displaced by the "Conan MB antibody" (ATCC HB 8939) from the binding to CK-MB and isolating the monoclonal antibody from the cloned cells or their culture supernatant by known methods.

In a particular embodiment of the process according to the invention those clones are selected which produce an antibody which has an association constant for binding to CK-MB of at least $1\times10^5$ mol$^{-1}\times$1$\times$sec$^{-1}$ or a dissociation constant of less than $4\times10^{-4}$ sec$^{-1}$ or an affinity constant of at least $1\times10^8$ mol$^{-1}\times$1.

With the aid of the monoclonal antibodies according to the invention those immunological test procedures for the diagnostic determination of CK-MB are also feasible which require two specific antibodies for CK-MB of high affinity against different epitopes.

The invention therefore in addition concerns the use of a monoclonal antibody according to the invention to determine CK-MB in a diagnostic test.

This determination can be carried out by means of all conventional immunoassays such as e.g. ELISA, fluorescent immunoassay, electrochemiluminescent immunoassay (WO 86/02734, WO 87/06706, WO 92/14138), radioimmunoassay, fluorescence polarization immunoassay, CEDIA (Henderson et al., Clin. Chem. 32 (1986), 1637–1641 and U.S. Pat. No. 4,708,929), IEMA or EMIT. In this case the test can be carried out as a homogeneous test e.g. via a competitive immunoassay as well as a heterogeneous test. Tests are preferably carried out with immobilization of one of the reaction partners. A determination by means of the so-called LPIA test (latex particle immunoassay) is preferred. For this two antibodies against different epitopes of CK-MB are firstly bound to a universal streptavidin latex matrix. The determination of CK-MB is then carried out by incubating these conjugates with the sample or with a CK-MB standard and measuring the increase in absorbance caused by the agglutination.

The invention therefore also concerns a method for the diagnostic detection of CK-MB in a homogeneous diagnostic test in which at least one antibody according to the invention is bound to a latex particle and, after incubation with the sample solution and with a further latex-bound antibody which binds to CK-MB without displacing the first antibody from its binding to CK-MB, the agglutination of the latex-bound antibody is determined as a measure of the concentration of CK-MB in the sample.

In this case a serum sample is usually used as the sample solution. In principle any antibody which reacts with CK-MB, i.e. also an antibody against the B or M subunit of creatine kinase, can be used as the second antibody bound to the latex particle. However, a high affinity antibody according to the invention against a conformation epitope of CK-MB is preferably used as the second latex-bound antibody. An antibody which is produced by the hybridoma cell line DSM ACC 2058, DSM ACC 2060 or DSM ACC 2168 is particularly preferably used as one of the two latex-bound antibodies. In this case the antibodies can be used as complete antibodies or as functional antibody fragments. Fab' fragments are preferably used.

In addition the invention concerns a method for detecting CK-MB in a homogeneous diagnostic test according to the CEDIA method in which an antibody according to the invention is used. In the CEDIA method particular enzymes such as β-galactosidase are used for the test which are present as two components each of which is enzymatically inactive, a large polypeptide (enzyme acceptor EA) and a small polypeptide (enzyme donor ED). These components associate spontaneously to form the enzymatically active protein. A peptide antigen, which in the case of CK-MB is this isoenzyme or a fragment thereof which contains the CK-MB specific epitopes, is bound to ED in such a way that it does not hinder the association of ED with EA. This association is inhibited when an antibody against the peptide antigen binds to the peptide antigen-ED complex. No active enzyme can be formed in a reagent solution in which EA, peptide antigen-ED complex and a peptide antigen-specific antibody are present. After addition of the sample solution which contains peptide antigens or, in the case of the CK-MB test, the CK-MB isoenzyme, CK-MB competes with the peptide antigen-ED complex for binding to the antibody according to the invention which enables the active ED/EA complex to form. The measured signal is thus proportional to the amount of CK-MB isoenzyme present in the sample. In the CEDIA method an antibody which binds to CK-MB in an equivalent manner to the monoclonal antibodies DSM ACC 2057 or DSM ACC 2059 and has an affinity constant of at least $1\times10^8$ $mol^{-1}\times1$ for CK-MB is well suited. The monoclonal antibody DSM ACC 2059 is particularly preferred which has a particularly high affinity constant of $7.0\times10^8$ $mol^{-1}\times1$.

The invention in addition concerns a method for the diagnostic detection of CK-MB by a sandwich assay in which at least one antibody according to the invention is bound to a solid phase, is incubated with the sample solution and with a further labelled antibody which binds to CK-MB without displacing the first antibody from its binding to CK-MB and after separating the solid and liquid phase, the label is determined in one of the two phases as a measure of the concentration of CK-MB in the sample. In this case an antibody is preferably used as one of the two antibodies which is produced by the hybridoma line DSM ACC 2058, DSM ACC 2060 or DSM ACC 2168.

Immobilization of the first antibody to the solid phase is achieved in a manner known to a person skilled in the art. The antibody is preferably biotinylated and bound to a solid phase coated with streptavidin. The second antibody is labelled in a conventional manner e.g. by direct labelling with an enzyme, a fluorescent or chemiluminescent dye or by binding a further antibody which is directed towards the second antibody and which has been labelled in an appropriate manner.

Detection by means of an electrochemiluminescent (ECL) immunoassay as described in WO 85/02734, WO 87/06706 or WO 92/14138 is also preferred. For this an antibody against CK-MB is firstly bound to a magnetic particle. The binding is preferably achieved by means of streptavidin and biotin. Streptavidin-coated magnetic particles and a biotinylated CK-MB antibody are used. The second antibody against CK-MB according to the invention should recognize a different epitope from the first antibody. This second antibody is coupled to the label. An electrochemiluminescent compound as described in WO 86/2734 and WO 87/06706 is used as the label. Tris-(bispyridyl)ruthenium is preferably used as the label. The label is coupled to the antibody according to methods of the state of the art. Incubation of the two antibodies according to the invention with the sample and the magnetic particles can take place simultaneously or successively. An instrument as described in WO 90/11511 is used for the measurement.

In the ECL immunoassay a first antibody is preferably used which binds to CK-MB in an equivalent manner to the monoclonal antibodies DSM ACC 2059 or DSM ACC 2057. The second antibody binds to another epitope and preferably in a manner equivalent to the monoclonal antibody DSM ACC 2058.

In the sandwich immunoassay the use of two monoclonal antibodies both of which bind to the CK-MB isoenzyme but not to the B or M subunit alone of the CK-MB isoenzyme and not substantially to the CK-MM and CK-BB isoenzymes and which do not compete with one another for the same binding site on CK-MB and at least one of which has an affinity constant of at least $1\times10^8$ $mol^{-1}\times1$ for CK-MB has proven to be particularly advantageous. At least one of these antibodies has particularly preferably an association constant of at least $1.9\times10^5$ $mol^{-1}\times1\times sec^{-1}$.

The aforementioned hybridoma cell lines DSM ACC 2059, DSM ACC 2057, DSM ACC 2058 and DSM ACC 2060 according to the invention were deposited on 03.02.1993 and the hybridoma cell line DSM ACC 2168 was deposited on the 19.04.1994 at the "Deutsche Sammlung für Mikroorganismen unol Zellkulturein GmbH", Mascheroder Weg 1b, D-38124 Braunschweig.

The invention is elucidated in more detail by the following examples.

EXAMPLE 1

Production of monoclonal antibodies against the CK-MB isoenzyme a) Immunization of mice 12 week old A/J mice are initially immunized intraperitoneally with 100 μg CK-MB (Aalto Co. Dublin). This is followed after 6 weeks by two further intraperitoneal immunizations at monthly intervals. In this process each mouse is administered 100 μg CK-MB adsorbed to aluminium hydroxide (Paesel Company, Frankfurt) and $10^9$ germs of Bordetella pertussis (Behring Co. Frankfurt). Subsequently the last two immunizations are carried out intravenously on the 3rd and 2nd day before fusion using 100 μg CK-MB in PBS buffer for each.

b) Fusion and cloning

Spleen cells of the mice immunized according to 1. are fused with myeloma cells according to Galfré, Methods in Enzymology 73, 1981, 3. In this process ca. $1*10^8$ spleen cells of the immunized mouse are mixed with $2*10^7$ myeloma cells (P3X63-Ag8-653, ATCC CRL1580) and centrifuged (10 min at 300 g and 4° C.). The cells are then washed once with RPMI 1640 medium without foetal calf serum (FCS) and centrifuged again at 400 g in a 50 ml conical tube. The supernatant is discarded, the cell sediment is gently loosened by tapping, 1 ml PEG (molecular weight 4000, Merck, Darmstadt) is added and mixed by pipetting. After 1 min in a water-bath at 37° C., 5 ml RPMI 1640 without FCS is added dropwise at room temperature within a period of 4–5 min. Afterwards 5 ml RPMI 1640 containing 10% FCS is added dropwise within ca. 1 min, mixed thoroughly, filled to 50 ml with medium (RPMI 1640+10% FCS) and subsequently centrifuged for 10 min at 400 g and 4° C. The sedimented cells are taken up in RPMI 1640 medium containing 10% FCS and sown in hypoxanthine-azaserine selection medium (100 mmol/l hypoxanthine, 1 μg/ml azaserine in RPMI 1640+10% FCS). Interleukin 6 (Boehringer Mannheim GmbH, Cat. No. 1271 172, 100 U/ml) is added to the medium as a growth factor.

After ca. 10 days the primary cultures are tested for specific antibody synthesis and cross-reaction (see example 2). CK-MB-positive primary cultures which do not show a substantial cross-reaction with the isoenzymes CK-MM and CK-BB are cloned in 96-well cell culture plates by means of a fluorescence activated cell sorter. In this process interleukin 6 (Boehringer Mannheim GmbH, Cat. No. 1271172, 100 U/ml) is added to the medium as a growth additive. Of those clones which produce an antibody against a conformation epitope of CK-MB (determined according to example 2), those cultures are selected which have an antibody with an affinity of at least $9\times10^7$ $mol^{-1}\times l$ for CK-MB (determined according to example 3) and/or an antibody which recognizes a different epitope than the "Conan MB antibody" (determined according to example 4).

c) Immunoglobulin isolation from the cell culture supernatants

The hybridoma cells obtained are sown at a density of $1\times10^5$ cells per ml in RPMI 1640 medium containing 10% FCS and proliferated for 7 days in a fermenter (Thermodux Co., Wertheim/Main, Model MCS-104XL, Order No. 144-050). On average concentrations of 100 μg monoclonal antibody per ml are obtained in the culture supernatant. Purification of this antibody from the culture supernatant is carried out by conventional methods in protein chemistry (e.g. according to Methods in Enzymology 121 (1986), 587–695).

EXAMPLE 2

Determination of the specificity of the antibodies produced

In order to determine the specificity of the antibodies in the culture supernatant of the hybridoma cells, the reactivity with CK-MB, CK-MM and CK-BB is determined in three parallel ELISA mixtures. For this 96-well microtitre plates (Nunc) are firstly coated with 200 μl/well thermo-BSA-streptavidin (10 μg/ml coating buffer=0.2 mol/l sodium carbonate/bicarbonate, pH 9.3–9.5, Boehringer Mannheim GmbH, Cat. No. 0726559) (1 h incubation at room temperature while shaking) and washed once with 0.9% NaCl/0.05% TWEEN 20 (polysorbate 20 or sorbitan monolaurato ethoxylate). CK-MB, CK-MM and CK-BB (Aalto Co. Dublin, Cat.No. 10901, 10217 and 10803) are biotinylated in parallel with D-biotinyl-ε-amido caproic acid-N-hydroxysuccinimide ester (Boehringer Mannheim GmbH, Cat.No. 01008960) according to the manufacturer's instructions. The biotinylated creatine kinase isoenzymes are taken up in a concentration of 250 ng/ml PBS containing 0.05% TWEEN 20/1% bovine serum albumin, 100 μl is added per well to the microtitre plates coated with thermo-BSA-streptavidin and incubated for 1 hour at room temperature while shaking. Subsequently they are washed with 3×0.9% sodium chloride/0.05% TWEEN 20. 100 μl of each of the antibody solutions to be examined is added in parallel experiments to a well coated with CK-MB, CK-MM or CK-BB and incubated for 1 hour at room temperature while shaking. After washing three times with 0.9% sodium chloride/0.05% TWEEN 20, 100 μl of a POD-labelled Fab fragment of a polyclonal antibody from sheep against mouse-Fc-γ (Boehringer Mannheim GmbH, Ident. No. 1047523 corresponding to 100 mU) is added to detect bound antibody from the sample, incubated for 1 h at room temperature while shaking and subsequently washed three times with 0.9% sodium chloride/0.05% TWEEN 20. Finally 100 μl ABTS® is added to each well (Boehringer Mannheim GmbH, Cat.No. 1204521 and 1204530) and after 30 min at room temperature the absorbance at 450/490 nm is measured in a MR700 microplate reader from the Dynatech Company.

EXAMPLE 3

Determination of the affinity, association and dissociation constants and of the sandwich compatibility of the antibodies produced The determination of the affinity, association and dissociation constants and the sandwich compatibility of the antibodies produced is carried out according the BIAcore® system of the Pharmacia LKB Company. In this method the CK-MB isoenzyme is covalently bound and thus immobilized in the surface layer of a so-called sensor chip. When a solution of the antibody to be determined is passed over, during which the antibody is bound to the immobilized CK-MB by non-covalent interaction forces, the mass density in the surface layer increases. The increase in mass density can be monitored directly by means of surface plasmon resonance. A third and fourth reaction partner may additionally attach depending on the number of binding sites present on the immobilized reaction partner. Their binding can be observed with respect to kinetics and amount just as those of the first reaction partner.

All reaction partners with the exception of the covalently bound CK-MB can be detached by simple means without damaging CK-MB so that further binding experiments can be carried out on the same primary phase under identical boundary conditions.

In order to bind CK-MB to the surface layer of the sensor chip a solution of 20 µg/ml CK-MB (Alto, Lot No. 20410) in 10 mmol/l HEPES/3.4 mmol/l EDTA/150 mmol/l NaCl/ pH 7.4 is passed over a sensor chip at a flow rate of 2 µl/min.

Subsequently the following antibodies are added and the association or dissociation constants for binding to CK-MB as well as the affinity of the antibodies to CK-MB are determined by means of the BIAcore® system according to the manufacturer's instructions (Pharmacia LKB, Software Kinetic Evaluation Kit, Ident.No. BR-1000-19). The values determined in this manner for the antibodies according to the invention as well as for the "Conan MB antibody" ATCC HB 8939 and for a commercially available antibody against CK-MB (BP 172-A2720 of Bios Pacific) are summarized in Table 1.

TABLE 1

| Antibody | Association constant $(mol^{-1} \times 1 \times sec^{-1})$ | Dissociation constant $(sec^{-1})$ | Affinity constant $(mol^{-1} \times x \times 1)$ |
|---|---|---|---|
| DSM ACC 2059 | $1.9 \times 10^5$ | $2.7 \times 10^{-4}$ | $7.0 \times 10^8$ |
| DSM ACC 2057 | $4.4 \times 10^4$ | $1.8 \times 10^{-4}$ | $2.4 \times 10^8$ |
| DSM ACC 2058 | $1.8 \times 10^5$ | $3.5 \times 10^{-3}$ | $5.0 \times 10^7$ |
| DSM ACC 2060 | $6.4 \times 10^4$ | $2.9 \times 10^{-3}$ | $2.2 \times 10^7$ |
| ATCC HB 8939 | $3.4 \times 10^4$ | $4.1 \times 10^{-4}$ | $8.2 \times 10^7$ |
| BP173-A2720 (Bios Pacific) | $4.1 \times 10^4$ | $1.7 \times 10^{-3}$ | $2.5 \times 10^7$ |

In an analogous manner it is possible to determine the sandwich compatibility of the antibodies according to the invention by means of the BIAcore® system. For this a polyclonal antibody against murine IgG1 or a polyclonal antibody against murine Fcγ is firstly immobilized as a capture antibody on the sensor chip. Subsequently it is firstly loaded with a first antibody to be examined against CK-MB up to an amount of 1000 resonance units and capture antibodies which are still free are blocked by passing over an immunoglobulin which does not cross react with CK-MB. After passing over a solution containing CK-MB the association is monitored until equilibrium is achieved and subsequently the potential sandwich partner to be examined is added and the association of the sandwich complex is monitored until equilibrium. In this process it has turned out that the combinations of antibodies according to the invention listed in the following Table 2 are suitable for a CK-MB test. Combinations of DSM ACC 2057 with DSM ACC 2058 or DSM ACC 2060 or the combinations of DSM ACC 2059 with DSM ACC 2058 or DSM ACC 2060 have proven to be particularly suitable. In contrast only a weak sandwich formation could be observed with the previous standard antibody against CK-MB (ATCC HB 8939) which must be regarded as being inadequate for a reliable diagnostic test.

TABLE 2

| first antibody | potential second antibody for a sandwich |
|---|---|
| DSM ACC 2057 | DSM ACC 2058 |
|  | DSM ACC 2060 |
| DSM ACC 2059 | DSM ACC 2058 |
|  | DSM ACC 2060 |
| DSM ACC 2059 | DSM ACC 2057 |

Using the monoclonal antibodies DSM ACC 2057 and DSM ACC 2059 a triplet formation can also be achieved with the combinations given in the following Table 3 in which three antibodies bind to CK-MB. By this means it is possible to achieve a further increase in sensitivity and specificity compared with the normal sandwich assay.

TABLE 3

| first antibody | second antibody | third antibody |
|---|---|---|
| DSM ACC 2057 | DSM ACC 2058 | DSM ACC 2060 |
| DSM ACC 2059 | DSM ACC 2058 | DSM ACC 2060 |

EXAMPLE 4

Determination of the epitope overlap of antibodies against CK-MB

A competitive enzyme immunoassay is carried out to determine the epitope overlap of an antibody with an antibody according to the invention. For this CK-MB is firstly biotinylated with D-biotinyl-ε-amidocaproic acid-N-hydroxysuccinimide ester (Boehringer Mannheim GmbH, Cat.No. 1008960) according to the manufacturer's instructions. 300 ng of this biotinylated antigen in a volume of 100 µl PBS is bound to a streptavidin-coated microtitre plate (manufactured according to EP-A 0 344 578) by incubating for 1 hour at room temperature. After washing three times with PBS/0.05% TWEEN 20 it is simultaneously incubated with the reference antibody (e.g. DSM ACC 2059) which was labelled with peroxidase (final concentration 52 mU/ml) and with the antibody to be assessed. After a further threefold washing with PBS/0.05% TWEEN 20, it is incubated for 30 minutes at room temperature with the enzyme substrate solution ABTS® in a buffer containing sodium perborate and subsequently the absorbance at 405 nm is measured as a measure of the amount of bound POD-labelled monoclonal antibody. This value is compared with the absorbance that is obtained on incubation with the labelled monoclonal antibody alone. If a competition of at least 50% is detectable up to a $10^5$-fold excess of antibody under assessment over the labelled antibody, an epitope overlap is present.

The antibodies from the cell lines DSM ACC 2057 and DSM ACC 2059 showed a strong competition, which means that they recognize or bind to the same epitope that is also recognized by the so-called "Conan" antibody. The antibodies from the cell lines DSM ACC 2058, DSM ACC 2060 and DSM ACC 2168 do not compete with the antibodies from the other two cell lines (DSM ACC 2057 and DSM ACC 2059). With the exception of the two antibodies from the cell lines DSM ACC 2060 and DSM ACC 2168, these three antibodies show no competition. The antibodies DSM ACC 2060 and DSM ACC 2168 show a low competition which leads to the conclusion that the two epitopes slightly overlap. It is therefore not advantageous to use these two antibodies for example together in a sandwich test. However, in combination with another antibody according to the invention each of these antibodies can be used very well.

EXAMPLE 5

Determination of CK-MB by means of a LPIA test

Firstly two antibodies according to the invention which are suitable for a sandwich test are selected (see example 3) and Fab' fragments are biotinylated according to the instructions in EP-A 0 464 554.

20 μl in each case of a CK-MB standard (0, 110 and 220 ng CK-MB/ml human serum) or the sample to be analysed are pipetted at time point t=0 min as a sample on a Hitachi 717 photometer. Immediately 330 μl reagent 1 (reaction buffer=50 mmol/l Tris/HCl, pH 7.5, 75 mmol/l sodium chloride, 3% PEG 35,000, 1% Pluronic F68, 0.1% BRIJ 35 (dodecyl(polyethylene glycolether)$_n$ wherein n is 0–23) and 0.1% sodium azide) is pipetted automatically to this by the instrument. At time point t=4.5 min 50 μl reagent 2 (latex suspension; 0.083% steptavidin latex in each case precoated with 1.6 μg antibody/ml in 200 mmol/l glycine, pH 7.5, 2% sucrose, 0.5% BSA I (BSA purity level I, 0.1% sodium azide) is added by the instrument. Subsequently the increase in agglutination is measured bichromatically at 340 nm (main wavelength) and 700 nm (secondary wavelength) (measuring temperature 37° C.). The difference in absorbance between the time points t=5.3 min and t=9.5 min is used as the signal parameter. In this case the combination of the antibodies DSM ACC 2059 and DSM ACC 2058 has proven to be particularly suitable (corresponding to a high dynamic range (difference between the second measured value and the blank value) of 342 mA as well as to a high initial increase in the calibration curve (2.3 mA×ml/ng).

EXAMPLE 6

Determination of CK-MB by a sandwich test using the electrochemiluminescent method The ECL method was carried out according to WO 86/02734, WO 87/06706 and WO 92/14138. The monoclonal antibody DSM ACC 2059 was biotinylated according to methods of the state of the art (solution 2). The monoclonal antibody DSM AC 2058 was ruthenylated with DSS (disuccinyl substrate) ((Tris)(2,2'-bipyridiyl) ruthenium chloride hexahydrate) (solution 3). Both antibodies were incubated for 5 minutes with the sample containing CK-MB in solution 1 and subsequently streptavidin-coated magnetic particles (Dynabeads M-280 streptavidin from the Deutsche Dynal GmbH Company, Germany) were added (solution 4) and it was again incubated for 5 minutes.

The reaction is terminated by aspirating the reaction mixture in the measuring cell. An Origen 1.0-instrument from the Igen Company USA was used. In the measuring chamber the magnetic particles are retained on the electrode by a magnet. The residual reaction mixture is aspirated and the measuring chamber is filled with assay buffer (solution 5). The light emission is stimulated by applying an electrical potential.

The following solutions were used:#
Solution 1:
  Incubation buffer:
  100 mM sodium phosphate pH 7.0
  0.1% BSA
  0.1% methyl isothiazolone
  0.1% sodium benzoate
Solution 2:
  biotinylated MAB DSM ACC 2059
  2 μg/ml in incubation buffer
Solution 3:
  ruthenium-bispyridyl-labelled MAB DSM ACC 2058
  2 μg/ml in incubation buffer
Solution 4:
  500 μg/ml streptavidin-coated magnetic particles in:
  50 mM Hepes, 0.1% BSA, 0.1% THESIT(polydocanole or dodecyl poly(ethylene glycol etheryn wherein n is 0–20) 0.1%
  chloroacetamide, 0.01% methyl isothiazolone, pH 7.0
Solution 5:
  Assay buffer: pH 6.8
  0.16M Tris-propylamine, 0.2M di-potassium hydrogen phosphate, 0.1% polydocanol (THESIT), 0.1% Oxaban A.

We claim:
1. A method for determining the presence or amount of CK-MB in a sample, comprising:
  a) contacting the sample with
    i) at least one first monoclonal antibody that specifically binds CK-MB, wherein said antibody is immobilized on a latex particle, and
    ii) a further latex-bound second monoclonal antibody that specifically binds CK-MB, wherein said second antibody binds to a different epitope than said first antibody and does not displace the first monoclonal antibody from its binding to CK-MB, wherein said first and second monoclonal antibodies bind to said CK-MB but not to the individual B or M subunits of CK-MB and not substantially to CK-MM and CK-BB, and wherein one of the latex-bound antibodies is produced by hybridoma line DSM ACC 2058 or DSM ACC 2060, or binds to the same epitopes as antibodies produced by hybridoma line DSM ACC 2058 or DSM ACC 2060;
  b) measuring any increase in agglutination as a measure of the amount or presence of CK-MB in the sample.

2. A sandwich immunoassay for determining the presence or amount of CK-MB in a liquid sample, comprising:
  a) contacting the liquid sample with
    i) a first monoclonal antibody immobilized on a solid phase, wherein said first antibody specifically binds to said CK-MB, and
    ii) a second monoclonal antibody conjugated to a label, wherein said second antibody specifically binds to said CK-MB, and wherein said second antibody binds to a different epitope than said first antibody and does not displace the first monoclonal antibody from its binding to CK-MB, and wherein said first and second monoclonal antibodies bind to said CK-MB but not to the individual B or M subunits of CK-MB and not substantially to CK-MM and CK-BB, and wherein one of the latex-bound antibodies is produced by hybridoma line DSM ACC 2058 or DSM ACC 2060, or binds to the same epitopes as antibodies produced by hybridoma line DSM ACC 2058 or DSM ACC 2060;
  b) separating the solid and liquid phases;
  c) measuring the label present in either the separated solid or liquid phase;

d) correlating the amount of measured label to the presence or amount of said CK-MB in said liquid sample.

3. The method according to claim 1, wherein at least one of the monoclonal antibodies has an affinity constant of at least $1\times10^8$ $mol^{-1}\times l\times sec^{-1}$ to said CK-MB and is produced by hybridoma line DSM ACC 2058 or DSM ACC 2060.

4. The method of claim 2 wherein at least one of the monoclonal antibodies has an affinity constant of at least $1\times10^8$ $mol^{-1}\times l\times sec^{-1}$ to said CK-MB and is produced by hybridoma line DSM ACC 2058 or DSM ACC 2060.

* * * * *